(12) United States Patent
Assis et al.

(10) Patent No.: US 8,700,128 B2
(45) Date of Patent: Apr. 15, 2014

(54) METHOD AND APPARATUS FOR POSITIONING A BIVENTRIVULAR PACEMAKER LEAD AND ELECTRODE

(75) Inventors: Tsuriel Assis, Rehovot (IL); Moshe Klaiman, Gadera (IL); Michael Zarkh, Givat Shmuel (IL)

(73) Assignee: Paieon Inc. NY (US)

( * ) Notice: Subject to any disclaimer, the term of this patent is extended or adjusted under 35 U.S.C. 154(b) by 858 days.

(21) Appl. No.: 11/912,840

(22) PCT Filed: May 3, 2005

(86) PCT No.: PCT/IL2005/000462
§ 371 (c)(1),
(2), (4) Date: Apr. 10, 2008

(87) PCT Pub. No.: WO2006/117773
PCT Pub. Date: Nov. 9, 2006

(65) Prior Publication Data
US 2009/0216112 A1    Aug. 27, 2009

(51) Int. Cl.
*A61B 6/00*          (2006.01)
(52) U.S. Cl.
USPC ........... 600/424; 600/407; 600/426; 600/301; 600/309; 382/128; 382/154; 382/294
(58) Field of Classification Search
USPC .................. 600/407, 424; 382/128, 130, 131; 607/9, 123, 129
See application file for complete search history.

(56) References Cited

U.S. PATENT DOCUMENTS

| | | | |
|---|---|---|---|
| 6,195,577 B1 | 2/2001 | Truwit | |
| 6,733,500 B2 * | 5/2004 | Kelley et al. | 606/41 |
| 7,327,872 B2 * | 2/2008 | Vaillant et al. | 382/154 |
| 7,346,381 B2 * | 3/2008 | Okerlund et al. | 600/407 |
| 7,499,743 B2 * | 3/2009 | Vass et al. | 600/426 |
| 7,534,207 B2 * | 5/2009 | Shehada et al. | 600/309 |
| 7,627,373 B2 * | 12/2009 | Girouard et al. | 607/9 |
| 7,695,512 B2 * | 4/2010 | Lashinski et al. | 623/2.37 |
| 2002/0057825 A1 | 5/2002 | Evron et al. | |
| 2004/0236192 A1 * | 11/2004 | Necola Shehada et al. | 600/301 |
| 2005/0060030 A1 * | 3/2005 | Lashinski et al. | 623/2.37 |
| 2006/0134071 A1 * | 6/2006 | Ross et al. | 424/93.7 |
| 2006/0134079 A1 * | 6/2006 | Sih et al. | 424/93.21 |
| 2006/0136027 A1 * | 6/2006 | Westlund et al. | 607/123 |
| 2006/0136028 A1 * | 6/2006 | Ross et al. | 607/129 |
| 2009/0163782 A1 * | 6/2009 | Shehada et al. | 600/301 |

FOREIGN PATENT DOCUMENTS

WO    01/85030 A    11/2001
WO    2005/008583 A    1/2005

\* cited by examiner

*Primary Examiner* — Baisakhi Roy
(74) *Attorney, Agent, or Firm* — Soroker Agmon

(57) ABSTRACT

An apparatus and method for placing a device in a body area of a patient, by: tracking the device over a 3-dimensional model of the body area; activating the device at different locations in the body area; measuring the response signal or parameter caused by the activation; storing the locations as well as the response signals; choosing an optimal location for the device base in the stored response signals and navigating the device to the optimal location.

16 Claims, 2 Drawing Sheets

METHOD AND APPARATUS FOR POSITIONING A BIVENTRIVULAR PACEMAKER LEAD AND ELECTRODE

RELATED APPLICATIONS

The present invention relates to international patent application titled "METHOD AND APPARATUS FOR POSITIONING A DEVICE IN A TUBULAR ORGAN" submitted on Mar. 31, 2005 and assigned to the same assignee as the present invention, which is a continuation in part of U.S. patent application Ser. No. 10/451,543 titled "METHOD AND APPARATUS FOR POSITIONING AN OBJECT IN AN ARTERY" filed on Jul. 24, 2003 with priority dated Oct. 18, 2000, and a continuation in part of European patent application designated serial number 1980855.9 titled "METHOD AND APPARATUS FOR POSITIONING AN OBJECT IN AN ARTERY" filed on 30 Jul. 2003 with priority dated 18 Oct. 2000, the contents of which are incorporated herein by reference.

The present invention also relates to International patent application serial number PCT/IL01/00201 titled "SYSTEM AND METHOD FOR THREE-DIMENSIONAL RECONSTRUCTION OF AN ARTERY" filed on 2 Mar. 2001, the content of which is incorporated herein by reference.

BACKGROUND OF THE INVENTION

1. Field of the Invention

The present invention relates to medical systems in general, and to a method and apparatus for positioning a biventricular pacemaker in the heart, in particular.

2. Discussion of the Related Art

Many people worldwide suffer from abnormal heart rhythm, where the rhythm may be too rapid, too slow, or irregular. The abnormal heart rhythm can occur in response to an emotion or event. The heart may seem to skip a beat when a person is excited, or race when a person is nervous or afraid. These sensations are called palpitations. In such cases, palpitations are usually of no consequence. However, they can be symptoms of a disorder involving abnormal heart rhythm called an arrhythmia. The regular heart beat rhythm changes its rate in response to different activities. That is, the heart speeds up or slows down to adjust the amount of blood it pumps in response to the body's needs. Heartbeats are controlled by the heart's electrical system. Electrical currents are produced and coordinated by the heart's natural pacemaker (sinus or sinoatrial node), located in the upper right heart ventricle (right chamber). The electrical currents flow through the heart along specific pathways in the heart and at a controlled speed. They stimulate the heart to contract, producing each heartbeat. Certain hormones and nerve impulses from other parts of the body signal the heart when a change in heart rate is needed. Arrhythmias are more likely to develop as people age, particularly in those who have other heart disorders. In many people, arrhythmias occur from time to time (intermittently), and some arrhythmias gradually occur more and more often and may become constant. For most people, arrhythmias are harmless, but some arrhythmias have serious consequences, such as falls, motor vehicle accidents, heart failure and occasionally, sudden death. Arrhythmias are categorized partly by their speed, into bradycardias (Slow arrhythmias) and tachycardias (fast arrhythmias). Alternatively, arrhythmias can be categorized by the causing factor. Some problems such as premature atrial beats, supraventricular tachycardia, atrial flutter, and atrial fibrillation involve the upper chambers (atriums), other problems such as premature ventricular beats, ventricular tachycardia, and ventricular fibrillation result from problems in the lower chambers (ventricles). Yet other types of arrhythmias result from problems in initiating and conducting electrical currents including malfunction of the heart block or the heart's pacemaker, such as some cases of sinus bradycardia and sick sinus syndrome.

Some arrhythmias do not require specific treatment, and many other cases can be treated effectively. Sometimes arrhythmias occur less often or even stop when patients change certain aspects of their lifestyle, such as smoking, caffeine consumption, exercise, drugs or drugs doses or the like. In yet other cases, implanting artificial pacemakers is a common treatment. Artificial pacemakers are electronic devices that act in place of the heart's own pacemaker, by sending electrical signals to the heart, and thus causing the right side of the heart to contract. An artificial pacemaker consists of a generator which is an electronics box that produces and controls the pacing signals, and is implanted surgically, usually in a pocket under the skin located below the collarbone, and connected to the heart by insulating leads or wires running inside the veins. Each wire ends with an electrode which delivers the electrical excitation generated in the pacemaker and flowing through the leads to the heart. Standard pacemakers comprise two electrodes, one is placed at the right ventricle and the other at the right atrium. Some pacemakers are on all the time, overriding the electrical impulses generated by the heart. Other pacemakers let the heart beat naturally unless it skips a beat or begins to beat at an abnormal rate. Some pacemakers, called programmable pacemakers, can be adjusted to do either. Yet another type of pacemakers has the ability to adjust their rate to the need of the patient, beating quickly during exercise and slowly during rest.

In some cases, for example when the two ventricles of the heart do not pump together which happens in approximately 20 to 30 percent of patients with heart failure, a standard pacemaker does not provide adequate treatment to the problem, and bi-ventricular pacemaker is the recommended treatment. A biventricular pacemaker stimulates both the right and left sides of the heart simultaneously. This type of pacing is also called cardiac resynchronization therapy (CRT). By stimulating both ventricles, the device makes the walls of the right and left ventricles pump together again. The heart is thus resynchronized, pumping blood more efficiently while causing less wear and tear on the heart muscle itself. Similarly to standard pacemakers, the biventricular pacemaker consists of a generator, leads and electrodes. The insulating leads are attached to the generator and carry the electrical impulses from the generator to the heart, where they are delivered by the electrodes. The leads are threaded through the veins, usually the sub-clavian vein and/or cephalic vein, which can be easily accessed from the pocket under the skin. At the tip of each lead is an electrode that delivers the necessary electrical impulses to the heart. Thus, the electric impulses are created by the generator, carried by the leads and delivered by the electrodes to the heart. The biventricular pacemaker has an additional wire (lead) over the standard pacemakers, for pacing the left ventricle in addition to pacing the right ventricle and right atrium.

As with a standard pacemaker, the first and the second wires are threaded through the veins to the right ventricle and to the right atrium. In a bi-ventricular pacemaker, a third wire is implanted into the left ventricle, in a somewhat more complicated procedure. The third wire passes through the right atrium into a vein called the coronary sinus, which drains the heart of oxygen-poor blood, and then placed through a lateral branch to pace the left ventricle. The currently employed implantation procedure consists of the following steps: bringing the third lead into the coronary vein; optionally, inside the coronary vein tree, electric excitation is applied by the electrode in multiple locations and the electric response (ECG) is measured; when a location with acceptable electric response is identified, the electrode is mounted. Navigation in the coronary venous system is performed by using fluoroscopy with injections of iodine or any other contrast agent for viewing the coronary venous system. Because of the blood flow within the venous system, from distal areas to proximal areas, the contrast material disperses too fast in the veins. Therefore, sometimes a balloon is inflated inside the coronary sinus in order to stop the blood flow. The above procedure suffers from non optimal pacemaker positioning. Since it is difficult to navigate within the venous tree, which is different from patient to patient, and specifically, the interventionist might not be able to mark and return to a previously found location which yields better ECG response. Therefore, physicians usually stop searching once an acceptable location is found, although the location might be sub-optimal.

There is therefore a need in the art for a system that will enable a physician to test the electrical response resulting from positioning the third electrode of a bi-ventricular pacemaker at multiple locations, store the response together with the corresponding locations, and be able to navigate to a location that yields the best response.

SUMMARY OF THE PRESENT INVENTION

It is an object of the present invention to provide a novel method for determining a destination location position for a device within a body area of a patient, and navigating the device to the destination location. In accordance with the present invention, there is thus provided a method for determining a destination location for a device within a body area of a patient, the method comprising the steps of tracking the device within the body area using a model of the body area; at each of at least one location, obtaining one or more values of one or more parameters effected by the device, said values associated with said locations; storing the values and the associated locations; and determining a destination location associated with the values. The model can be a three-dimensional model, the body area can be the coronary venous system, the device can be an electrode of a bi-ventricular pacemaker and the parameter can be any of the group consisting of: electrocardiogram; heart rate; pulse; temperature; blood pressure and visual inspection. The method can further comprise the any if the steps of: generating the model of the body area, injecting the patient with contrast agent, assessing the quality of values of the parameters associated with the locations; presenting an image comprising elements from the model and the device to a user, navigating the device to the destination location, positioning the device at the destination location, activating the device in order to affect the values of the parameters. The method can further comprise the step of presenting to a user one or more locations in the body area together with the associated values of the parameters. The one or more locations can be presented on an image of the model, and can be marked on the image. The one or more locations can be presented to a user in a table. The step of locating the device within the model can comprise the steps of: obtaining an image of the device and the body area; and registrating the image with a model of the body area.

Another aspect of the present invention relates to an apparatus for determining a destination location for a device within a body area, the apparatus comprising a tracking component for tracking the device within the body area and a storing component for storing one or more values of one or more parameters, said one or more values associated with one or more locations within the body area. The model can be a three-dimensional model, the body area can be the coronary venous system, the device can be an electrode of a bi-ventricular pacemaker and the one or more parameters can be any of: electrocardiogram; heart rate; pulse; temperature; blood pressure; and visual inspection. The apparatus can further comprise one or more components from the group consisting of: a component for generating one or more models of the body area and a component for receiving one or more models of the body area. The apparatus can further comprise a registration component for registering an image depicting the device within the body area with one or more models of the body area. The apparatus can further comprise a first presentation component for presenting an image of a model of the body area together with an indication of the device, or a second presentation component for presenting the one or more values of the one or more parameters associated with the one or more locations within the body area. The apparatus can further comprise a connection component for receiving the one or more values of the one or more parameters from a measuring device. The apparatus can further comprise an assessment component for assessing the quality of the one or more values of the one or more parameters. The apparatus can further comprise a selecting component for selecting a location according to the associated one or more values of one or more parameters. The apparatus can further comprise a navigation component for navigating the device within the body area.

Yet another aspect of the present invention relates to a computer readable storage medium containing a set of instructions for a general purpose computer, the set of instructions comprising a tracking component for tracking the device within a body area; and a storing component for storing one or more values of one or more parameters, the one or more values associated with one or more locations within the body area.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

The disclosed invention offers an apparatus and method that overcome the disadvantage of the existing lead implantation procedure. The invention provides a physician with means to position a lead of a bi-ventricular pacemaker, connected to the electrode that should be placed in the left ventricle, to an optimal location through the coronary venous system. The invention preferably uses a 3-dimensional model of the coronary venous system, as generated from at least two angiographs, taken form two different angles, either prior to or during the implantation procedure. Alternatively, the apparatus can use a 3-dimensional model acquired from an external source. Then, the biventricular pacer lead is inserted into the coronary venous system, and one or more injections of contrast agent, such as iodine, are performed, followed by taking additional angiograms. The contrast agent angiogram enables the registration of the 3-dimensional model with the current angiograms (including iodine free angiograms, in which only opaque or semi-opaque objects are seen). The registration enables the superimposition and presentation of the 3-dimensional model together with the current location of the lead. Thus the lead can be tracked and navigated, either manually or by using any navigation system, within the venous system to any desired location. Throughout the navigation, the physician can apply electrical excitation through the electrode at any desired location. The system then measures a signal, such as an electrocardiogram (ECG) or any other applicable parameter, being the response to the electrical excitation, in the above chosen locations. The system further stores the locations, together with the corresponding response measurements. The system can display the locations and the corresponding signals over an image of the 3-dimensional reconstruction in any required form, such as a map, a table or the like. Once the location yielding the best available response is determined, the location is marked and possibly highlighted, together with the current location of the lead. Then the lead is tracked and navigated back to the designated location, either manually or by a navigation system. The lead is then mounted at the desired location, thus getting the best possible performance from the pacemaker.

Figure 1:
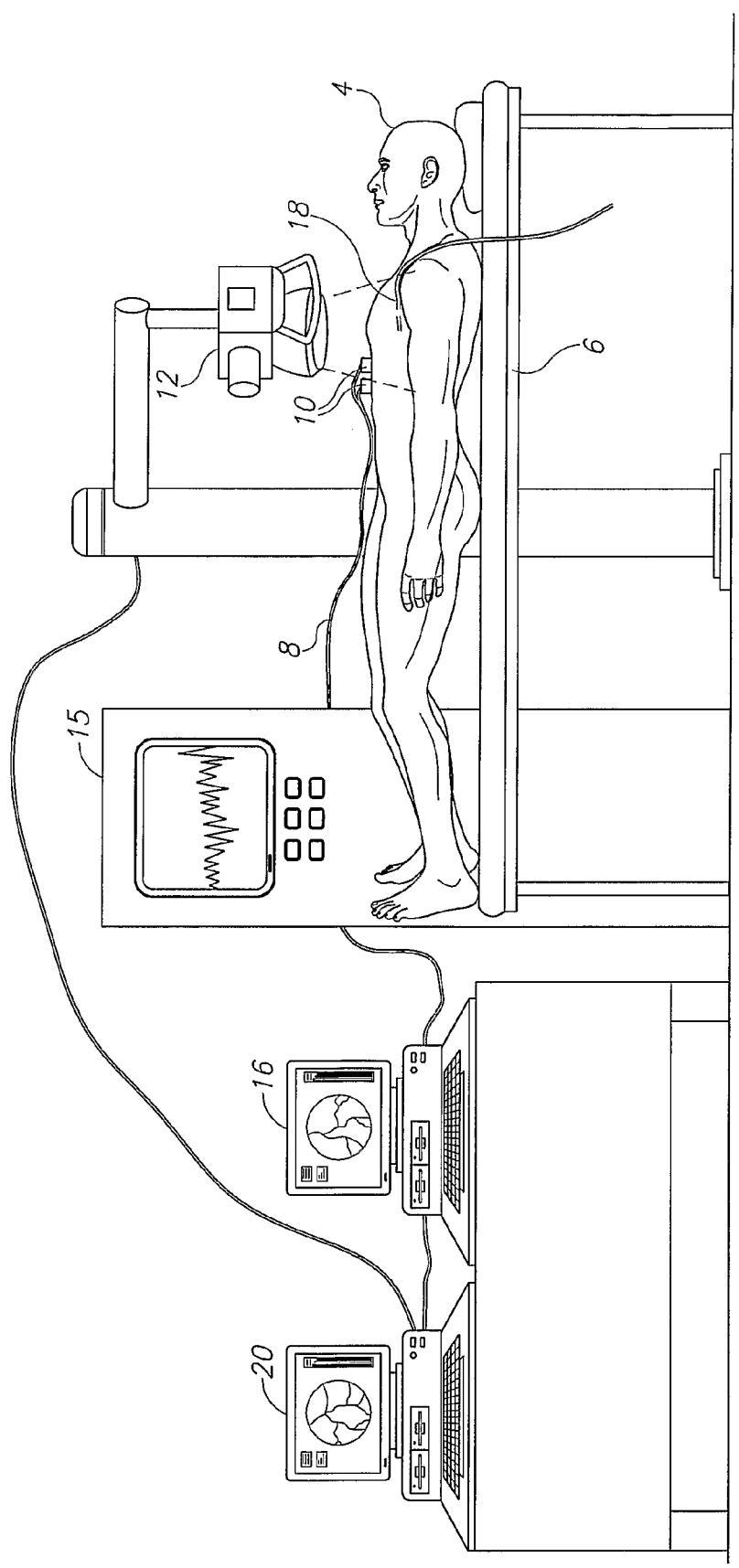
FIG. 1 is an illustration of a typical environment in which the proposed invention is used, in accordance with a preferred embodiment of the disclosed invention.

Referring now to FIG. 1 depicting an exemplary environment in which one preferred embodiment of the present invention is used. As shown in the figure in question, a patient subject 4 is lying down on a bed 6 in an operating room. An electrode lead 18 is inserted into the subject's body and is moved through the veins towards the area of the heart. A computerized angiography device 12 directed at the heart area is activated to produce one or more angiograms of the field of view. Since the electrode lead is preferably made of metal, it is visible in the angiograms. Device 12 connects to a work station 20, which receives and optionally presents angiograms from device 12. Work station 20 can also serve as an interface to other sources accessing the angiograms. The environment further comprises a measuring device 15, preferably an ECG, which comprises electrodes 10 placed on the patient's chest, and optionally a display showing the measured signal. In accordance with a preferred embodiment, the measurement results, preferably ECG are transferred from measuring device 15 to a work station 16. Work station 16 also connects and receives current angiograms from work station 20. The angiograms are preferably transferred to work station 16 via a transferring device such as a pre-defined I/O port (not shown), DICOM-implementing interface, or analog lines. Work station 16 preferably displays a previously generated or otherwise acquired 3-dimensional model of the venous system. Work station 16 also registers the model with the currently available angiograms, using one or more angiograms taken immediately after contrast agent injection. The current location of the lead, as determined through the registration process is marked on the model presentation. Optionally, work station 16 connects to measurement device 15, and stores the measured signal together with the relevant location of the lead. The display device of work station 16 preferably displays one or more images of the 3-dimensional model with the relevant ECG signal or another parameter associated with each relevant location of the lead as marked by the system, a table of the locations and associated signals or the like. Work station 16 is preferably a computing platform, such as a personal computer, a mainframe computer, or any other type of computing platform that is provisioned with a memory device (not shown), a CPU or microprocessor device (not shown), several I/O ports (not shown), input and output devices, preferably a keyboard, a mouse and a display device on which where the physician or another stuff member can view or manipulate the products of the applications. Alternatively, work station 16 delivers the output to another system via communication means. In an alternative embodiment, work station 16 can be a DSP chip (not shown), an ASIC device (not shown) storing the commands and data necessary to execute the methods of the present invention, or the like. Work station 16 can further include a storage device (not shown), storing the 3-dimensional model of the venous system and the relevant applications for registering, accessing the angiograms, tracking, navigating, connecting to measurement device 15 or storing the locations as well as the measured signals. The applications comprise a set of logically inter-related computer programs or components of computer components and associated data structures that interact to perform the abovementioned tasks.

Figure 2:
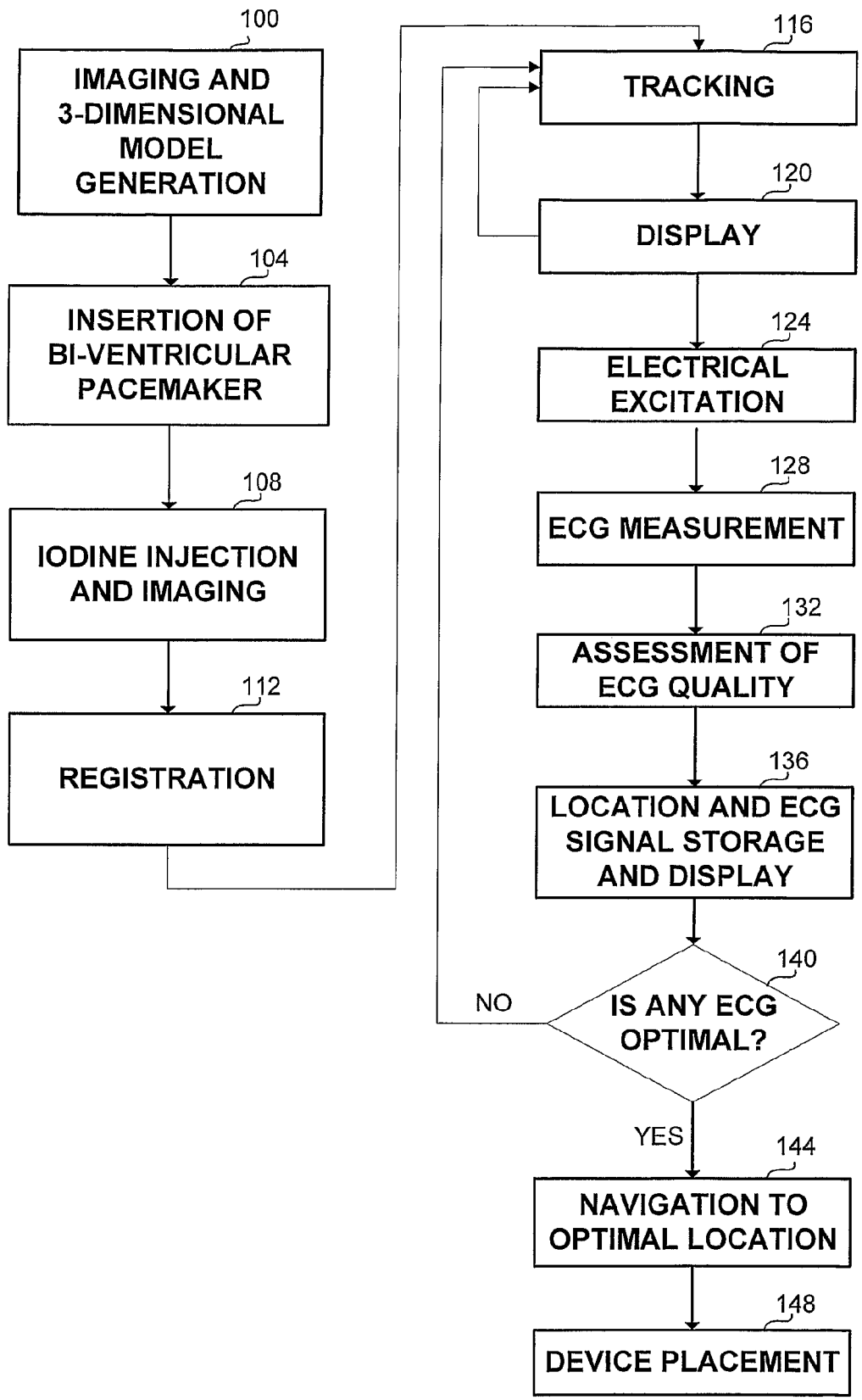
FIG. 2 is a flowchart of the main steps of the disclosed method, in accordance with a preferred embodiment of the present invention.

Referring now to FIG. 2, showing the main steps associated with the disclosed method, in accordance with a preferred embodiment of the disclosed invention. Imaging and 3-dimensional model generation step 100 is preferably performed prior to the implantation. At step 100, at least two cine angiograms of the coronary venous system are taken from at least two different perspectives, and a 3-dimensional model of the venous system is built. The images are taken after the patient has been injected with contrast agent, so that the veins are seen in the images. Optionally, the images are taken after a balloon is inserted and inflated inside the coronary sinus, so that the blood flow will not disperse the contrast agent before the images are taken. The model generation process is detailed in International patent application serial number PCT/IL01/00201 titled "SYSTEM AND METHOD FOR THREE-DIMENSIONAL RECONSTRUCTION OF AN ARTERY" filed on 2 Mar. 2001. Alternatively, step 100 is replaced by receiving a 3-dimensional model from an external source, such as CardiOp manufactured by Paieon of Rosh Ha'ayin, Israel. Step 100 can be performed immediately prior to the implantation procedure, or earlier than that, for example a few hours or a few days prior to the implantation. At step 104, an electrode of the bi-ventricular pacemaker which is designated to be inserted into the left ventricle, is inserted into a vein. The electrode is placed at the tip of an insulating lead which is used to navigate the electrode to the desired location. The vein which the electrode is inserted through is often the sub-clavian vein or the cephalic vein, which are easily accessible from the pocket under the skin that contains the generator of the pacemaker. At step 108, the patient is injected with contrast agent, such as iodine, and one or more fluoroscopic images are taken. The purpose of the images taken after the injection of the contrast agent is to bridge the gap between the 3-dimensional model showing only the venous system, and the current images taken during the implantation, which contain only the opaque lead but not the veins. The contrast agent images contain both the lead and the veins, which enables registration between the current images and the contrast agent images, and between the contrast agent images and the 3-dimensional model. The combination provides registration between the current images and the 3-dimensional model. The registration is performed at step 112, and provides the coordinates of the tip, thus enabling the display of the lead as captured in subsequent images, together with the 3-dimensional model, and displaying to the physician the exact location of the electrode. The registration process can be performed as an integral part of this invention, or by an external product. A method and apparatus for the registration process are detailed in International patent application titled "METHOD AND APPARATUS FOR POSITIONING A DEVICE IN A TUBULAR ORGAN" submitted on Mar. 31, 2005 incorporated herein by reference. Steps 108 and 112 might have to be repeated if the lead tip draws away from the location it was on when the first injection was performed, such that the registration error exceeds a predetermined threshold. At step 116, the lead tip is tracked and possibly navigated within the venous system by locating and following the tip in the angiograms. During the tracking process, the lead flows through the veins as seen in an image of the 3-dimensional model. The tracking of the tip is also detailed in the abovementioned International patent application. The navigation of the tip can be performed manually by the physician or automatically by any navigation system. At step 120, the tip's position is continuously displayed over an image of the 3-dimensional model. The combined display is the result of locating elements from the image captured during the navigation such as the lead tip in the 3-dimensional model of the venous system, superimposing them with elements from the model comprising the 3-dimensional model generated or acquired at step 100, and presenting the combined information to the user on one or more images. Steps 116 and 120 are repeated continuously until the tip arrives to a location which is a candidate for placing the electrode. At this time, step 124 is performed at which electrical excitation is introduced by the electrode to its surrounding, which is intended to be the left ventricle of the heart. The electrical excitation introduced at step 124 causes changes in the heart rhythm of the patient. The resulting heart rhythm depends, among other factors, on the location at which the excitation was introduced. In order to assess the effect of the excitation, at step 128 one or more relevant parameters of the patient, affected by the device are taken or measured, for example the ECG response. At step 132, the quality of the ECG, or the value of the one or more other parameters is assessed by the physician or by another means such as software, a device or the like. Step 132 is optional, and the ECG quality assessment can be skipped. At step 136, the ECG is stored together with the current location of the lead, and optionally presented with an image or information associated with the 3-dimensional model. If an ECG assessment was performed at step 132, and the ECG was assessed as having a poor quality, the storage and presentation can be skipped in order not to load the system with poor results. Optionally, the ECG can be stored and presented even if it is of poor quality so as to provide the physician with a full view of the heart area and the ECG behavior under electrical excitations at various locations. The ECG responses can be displayed as separate windows associated with specific markers on the image of the 3-dimensional model and containing data associated with the ECG. Alternatively, the ECG response can be displayed in the form of a table. The table can comprise, as a non-limiting example, one column denoting a location of the lead and another column denoting a graphic representation of the ECG signal, a pointer thereof, a general grade for the ECG or any other information associated with the ECG. The physician can also be given the option to add comments to the presentation. After one or more ECG results were assessed, at step 140 an assessment is performed whether an optimal location for the electrode had been found, or whether the physician should keep searching for one. The optimal location is preferably selected from the locations at which excitation was delivered and response measured, but can also be, for example, a location between two tested locations which the physician believes is optimal. The assessment which, if any, of the tested locations is optimal can be made by the physician, or by dedicated software, device, or the like. If no optimal location is determined, the process returns to step 116, the lead is navigated on, searching for additional locations to be tested until an optimal, or the best available location is determined. At step 144, once the location at which the excitation provides the best available response is selected or otherwise determined, the lead is navigated back to that destination location and mounted there. Similarly to step 116, the navigation can be performed either manually by a physician or by a dedicated system for example software, a device or the like. Such navigation system can receive instructions regarding forces, angles and directions for navigating the tip from its current location to the determined optimal location. At step 148 the electrode is placed and optionally fixed to the location which produces optimal response to electrical excitation.

The disclosed invention provides an apparatus and method for navigating a bi-ventricular pacemaker lead in the left ventricle venous system of the heart, for stimulating the left and the right ventricles of the heart simultaneously. The proposed method provides a way to generate an electrocardiograph map of the heart area, thus enabling a physician to choose the best location for the electrode. The physician does not have to settle for sub-optimal location of the electrode fearing that no better location would be found and he or she will not be able to return to the current location. Therefore the physician can keep searching until the best location is determined, at which stage the electrode is navigated to that location. Placing the electrode at the best location implies better treatment for the patient. Since the proposed method uses data about the venous system structure, substantially less contrast agent injections are required for tracking the electrode within the veins than would be required if the tip is to be tracked and navigated within an unknown morphology. Since using contrast material in the veins often necessitates the usage of an inflated balloon to stop blood flow in order to reduce material dispersion, eliminating or reducing the number of these procedures is beneficial is well.

It will be appreciated by persons skilled in the art that the above presented apparatus and method are not limited to the heart area or to the operation of placing a pacemaker. Rather, the apparatus and method can be used for navigating any device, such as an orthopedic device, a gynecologic device, or the like, within any area of the body. The method and apparatus can be used for any purpose, such as implantation, abscission, or the like, while measuring the performance of the device using any relevant signal or observation means.

It will be appreciated by persons skilled in the art that the present invention is not limited to what has been particularly shown and described hereinabove. Rather the scope of the present invention is defined only by the claims which follow.

What is claimed is:

1. A method for determining an implantation site for implanting a device within a coronary venous system of a patient, the method comprising the steps of:

tracking the device within the coronary venous system using a model of the coronary venous system;

electrically exciting the coronary venous system at multiple locations by means of said device;

obtaining values of an at least one physiological parameter effected by the device said electrically exciting at said multiple locations of the device within the coronary venous system, each of said values is associated with one of said multiple locations of the device;

storing said obtained values and their associated locations of the device; and determining the implantation site by comparing between said values and selecting a location associated with most appropriate value.

2. The method of claim 1 wherein the model is a three-dimensional model.

3. The method of claim 1 wherein the device is an electrode of a bi-ventricular pacemaker.

4. The method of claim 1 wherein the at least one physiological parameter is any of selected from the group consisting of: electrical measurement; heart rate; pulse; temperature; blood pressure.

5. The method of claim 1 further comprising the step of generating the model of the coronary venous system.

6. The method of claim 1 wherein the step of tracking the device within the coronary venous system comprises the steps of:
   obtaining an image of the device and the coronary venous system; and
   registering the image with the model of the coronary venous system.

7. The method of claim 1 further comprising the step of presenting an image comprising elements from the model and the device to a user.

8. The method of claim 1 further comprising the step of navigating the device to the determined implantation site.

9. The method of claim 1 further comprising the step of presenting to a user the multiple locations together with the associated values of the at least one parameter.

10. The method of claim 9 wherein the multiple locations associated with the values of the at least one parameter are presented on an image of the model.

11. The method of claim 1, further comprising injecting a contrast agent into the coronary venous system thereby enabling registration of an image depicting said device with said model.

12. A method for determining an implantation site for implanting a device within a coronary venous system of a patient and for navigating the device to said implantation site, the method comprising the steps of:
   tracking the device within the coronary venous system using a model of the coronary venous system;
   electrically exciting the coronary venous system at multiple locations by means of said device;
   at each one of said multiple locations of the device within the coronary venous system, obtaining values of at least one physiological parameter, each value of said values is associated with the location of the device during said electrically exciting the coronary venous;
   storing the obtained values and their associated locations of the device;
   determining the implantation site by comparing between said stored values and selecting a location associated with most appropriate value; and
   navigating the device from a current location to said implantation site.

13. The method of claim 12 wherein said device is an electrode of a bi-ventricular pacemaker.

14. The method of claim 13 further comprising a step of activating the device and wherein said at least one parameter is responsive to the activation of the device.

15. The method of claim 12 wherein the at least one physiological parameter is selected from the group consisting of: electrical measurement; heart rate; pulse; temperature; blood pressure.

16. The method of claim 12, further comprising injecting a contrast agent into the coronary venous system thereby enabling registration of an image depicting said device with said model.

* * * * *